United States Patent [19]

Rechenberg

[11] 4,172,298

[45] Oct. 30, 1979

[54] BREAST PROSTHESIS

[76] Inventor: Cornelius Rechenberg, Ganghofenstrasse 1, 8204 Brannenburg, Fed. Rep. of Germany

[21] Appl. No.: 800,384

[22] Filed: May 25, 1977

[30] Foreign Application Priority Data

Jun. 16, 1977 [DE] 06161977 .................. 7622581[U]

[51] Int. Cl.² .......................... A61F 1/00; A41C 3/10
[52] U.S. Cl. ...................................................... 3/36
[58] Field of Search .............. 3/36; 128/462, 378–381

[56] References Cited

U.S. PATENT DOCUMENTS

| | | | |
|---|---|---|---|
| 2,066,503 | 1/1937 | Wiggers | 3/36 |
| 2,867,818 | 1/1959 | Creamer | 3/36 |
| 3,494,365 | 2/1970 | Beals | 3/36 |
| 3,911,503 | 10/1975 | Hankin | 3/36 |
| 4,019,209 | 4/1977 | Spence | 3/36 |
| 4,086,666 | 5/1978 | Vaskys et al. | 3/36 |

FOREIGN PATENT DOCUMENTS 2457041 6/1976 Fed. Rep. of Germany ................ 3/36
1085676 7/1954 France ......................................... 3/36

OTHER PUBLICATIONS

Concise Guide to Biomedical Polymers, Their Design, Fabrication & Molding, by John W. Boretos, (Book), 1973, Charles C. Thomas—Publisher, Springfield, Ill. pp. 10–12 relied upon.

Primary Examiner—Ronald L. Frinks
Attorney, Agent, or Firm—Howard C. Miskin

[57] ABSTRACT

In a breast prosthesis comprising a one-piece flexible dished member which is free from air and has a shape simulating a female breast, said dished member comprises resiliently soft additive cross-linking two-component silicone rubber of an adhesive gelatinous consistency covered on each side by a plastics film, the plastics films being welded to each other along the rim of said dished member.

6 Claims, 2 Drawing Figures

BREAST PROSTHESIS

The invention relates to a breast prosthesis comprising a one-piece flexible dished member which is free from air and has a shape simulating a female breast.

About 4 to 5% of all women are taken ill with breast cancer which usually occurs between the 45th and 55th year of a patient's life span. In most cases, breast cancer makes it necessary to remove the breast, thereby making it necessary to wear breast prostheses in order to conceal the fact that the women in question has only one healthy normal breast.

U.S. Pat. No. 2,543,499 discloses a breast prosthesis comprising a one-piece flexible hollow member which is free from air, has a shape simulating a female breast and is filled with liquid, said hollow member comprising a double-walled dished member simulating the outer shape of a breast. Such air-free bag-like formations filled with liquid are heavier than a normal breast and, because of their sagging appearance, are generally declined because they look unnatural. A further disadvantage of liquid-filled prostheses is that the liquid filling migrates and could leak out if the surrounding envelope becomes damaged.

A breast prosthesis known from U.S. Pat. No. 2,851,692 consists either of a member made from an elastic foam-like material or of a hollow member consisting of a lightweight finely porous material containing a filling of elastic and foam-like material. The interior contains cylindrical cavities which are provided with movable weights. However, such prostheses are not sufficiently pliable in shape to simulate the appearance of a natural breast.

Other known breast prostheses filled with air or a granular material are also inadequate in simulating the appearance and general condition of a healthy breast.

In a breast prosthesis known from German Pat. No. 1,303,139, a moulded member of foam material having flat regions is surrounded at a spacing by a double-walled dished hollow member of plastics material which is connected to the moulded member only along its margin and is filled with a liquid. This breast prosthesis likewise has the disadvantage of a liquid filling and is not only complicated in construction but falls short of all the requirements of a natural appearance.

It is an object of the present invention to provide a breast prosthesis which, even during movement of the wearer, retains its natural appearance, has the mobility and softness of a healthy breast, can be worn comfortably and is simple to apply to the person.

According to the invention, the dished member of the breast prosthesis comprises resiliently soft additive cross-linking two-component silicone rubber of an adhesive gelatinous consistency covered on each side by a plastics film, the plastics films being welded to each other along the rim of said dished member.

The inventor has made the discovery that additive cross-linking silicone rubber is the ideal material for breast prostheses because it behaves in the same way as the living tissue of a breast. Additive cross-linking silicone rubber is a resiliently soft material of elastic gelatinous consistency and is self-restorative following deformation thereof to its original shape. By reason of the elastic softness as well as the mobility of the material, it is ideal for simulating a living breast. The material can be gently depressed in a resilient manner and will regain its original shape without exhibiting rubber-like springiness or permanent plastics deformation.

The invention employs silicone elastomers of the RTV (room-temperature-vulcanizing) type. They are prepared from linear organo-polysiloxanes containing alkenyl and Si-H compounds in the presence of precious metal catalysts such as platinum and platinum compounds by means of vulcanization at an elevated temperature, either pure or organo-siloxane resin-containing elastomers being created depending on the nature and number of the functional groups in the organo-polysiloxanes containing the Si—H compounds. Although the vulcanization of the linear organo-polysiloxanes in the presence of precious metal catalysts could also take place at room or body temperature, vulcanization at a slightly elevated temperature is particularly advantageous. The vulcanizing time of the catalyzed mixture amounts to from 1 to 6 hours at 40° to 120° C.

The two-component silicone rubber substance employed in accordance with the present invention is described in more detail in 'Chemiker-Zeitung', 97th year (1973, No. 4, pages 176–180). They are marketed by Wacker-Chemie-GmbH under the designation SLM 71158-3 (Komp. A) and SLM 71159-3 (Komp. B).

The additive cross-linking silicone rubber used in accordance with the invention is a resiliently soft mass of elastic gelatinous consistency and has approximately the same weight as living breast tissue so that it is ideally suitable for making a breast prosthesis.

Desirably the dished member defines a cavity at its rear. This cavity improves the wearing properties because the prosthesis is then better able to conform in shape to that of the body of the patient. The interior of the cavity of the prosthesis is also supported against the body of the patient, whereby the weld seams of the plastics films enveloping the prosthesis member are relieved of stresses. The cavity may exhibit a perimeter defined by a flat rim.

In use, it is possible that the cavity may give rise to the prosthesis exerting a suction effect against the body of the wearer. Although this effect enhances the connection between the prosthesis and the wearer, it could also result in the dished member becoming flattened. Further, it has been found that if the prosthesis adheres strongly to the wearer, perspiration may accumulate in the cavity, which would make wearing of the prosthesis uncomfortable. To improve comfort and avoid flattening, the rim of the dished member may be provided with at least one recess. This recess permits air to enter the cavity between the rim of the prosthesis and the body of the wearer, thereby eliminating the suction effect and flattening. Further, the formation or accumulation of condensation within the cavity is avoided by the venting brought about by said recess. The mobility of the prosthesis even helps to maintain a slight degree of circulation of the air that enters and leaves the cavity.

A good seating of the prosthesis on the body of the wearer is enhanced by the fact that it is held by a brassiere, the cavity adapting to the shape of the body of the wearer and being supported thereon.

It is also desirable if the recess in the rim of the dished member adjoins a flat channel that extends into the cavity. This channel ensures complete ventilation of the cavity and helps to avoid the aforementioned suction effect. The channel may be directed towards the apex of the cavity and become shallower so as to disappear completely at the apex.

The additive cross-linking silicone rubber used according to the invention is physiologically harmless. It does not have a tendency to migrate, nor does it react chemically when in contact with skin, perspiration or other substances. Since the material is not tear-proof and has an adhesive and slightly oily character, it has to be protected by an envelope of plastics film. Polyurethane film is particularly useful for the envelope because it is physiologically harmless, forms a barrier layer and has a skin-simulating character.

The prosthesis according to the invention can be applied very simply by inserting it in a brassiere. If it is shaped appropriately, the prosthesis may also be employed to give an enlarged appearance of a breast that is too flat.

An example of the invention will now be described with reference to the accompanying drawing, wherein.

Figure 1:
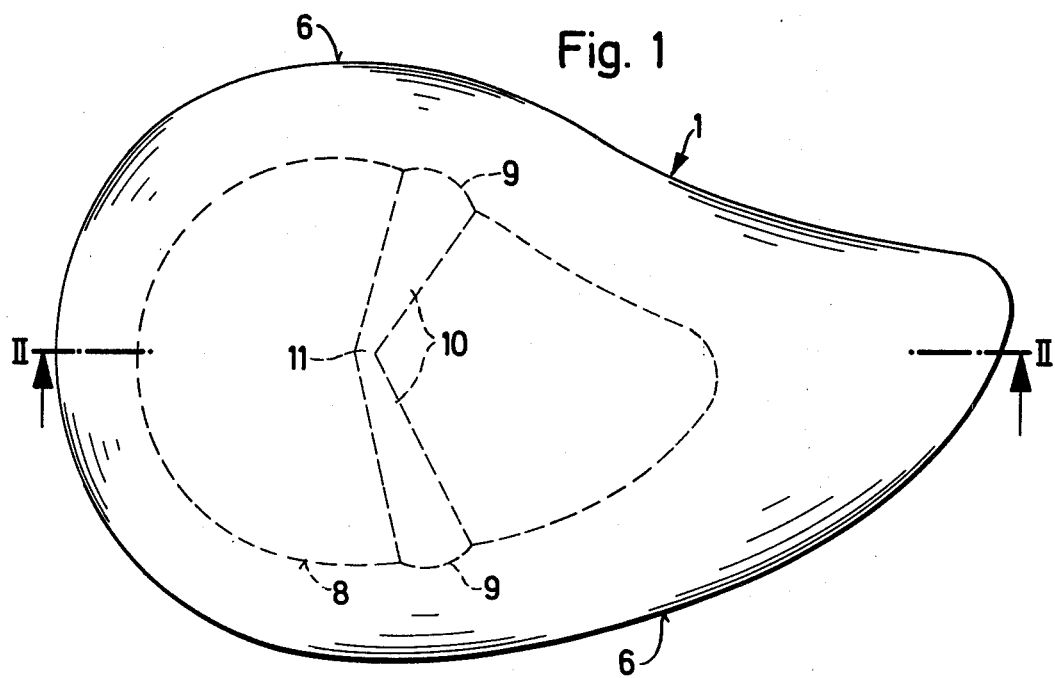
FIG. 1 is a plan view of a breast prosthesis.
Figure 2:
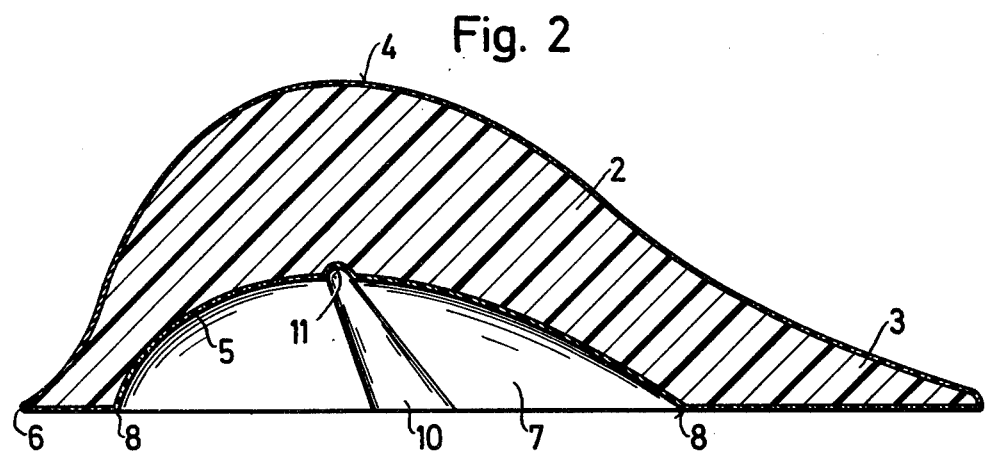
FIG. 2 is a section on the line II—II in FIG. 1.

The breast prosthesis 1 comprises a member 2 simulating the shape of a breast and consisting of additive cross-linking two-component silicone rubber. Adjoining the portion of the member 2 that actually simulates the shape of a breast, there is a portion 3 of the breast muscle extending towards the upper arm. The portion 3 helps to retain the prosthesis 1 in a brassiere.

On its surface and underface, the member 1 is covered by a respective plastics film 4, 5 of adequate strength and elasticity. The two films are interconnected along the outer peripheral edge 6 of the member 2 by means of a weld seam.

At the back, the member 2 has a cavity 7. The inner peripheral edge 8 of the prosthesis surrounding the cavity 7 comprises two recesses 9 from which channels 10 extend into the cavity 7, the edges 6 and 8 delineating a flat coplanar rim surrounding the cavity rear opening. The channels are directed towards the apex 11 of the cavity 7 and become shallower so as to disappear just before the apex.

I claim:

1. A breast prosthesis comprising a one-piece flexible dished member which is free from air and has a shape simulating a female breast and has a cavity in its rear having a rear peripheral rim, wherein said dished member comprises a body member formed essentially of a resiliently soft cross-linking two component silicone rubber of an adhesive gelatinous consistency and being self restorative following deformation thereof to its original shape and a plastics film covering each side of said body member, the plastics films being bonded to each other along said rim and said rim having at least one recess formed therein permitting the free flow between said rim and the body of the wearer of said prosthesis of air between said cavity and the exterior.

2. The breast prosthesis defined in claim 1, wherein said plastics material comprises polyurethane.

3. The breast prosthesis defined in claim 1, wherein said cavity is provided with at least one channel which becomes progressively shallower.

4. The breast prosthesis defined in claim 3, wherein said at least one channel extends from said rim towards the apex of said cavity.

5. The breast prosthesis defined in claim 4 wherein said channel becomes progressively narrower approaching said apex.

6. The breast prosthesis defined in claim 1 wherein said rim is substantially flat and planar.

* * * * *